United States Patent [19]
Chedid et al.

[11] Patent Number: 5,210,072
[45] Date of Patent: May 11, 1993

[54] MURAMYL DIPEPTIDE DERIVATIVES

[75] Inventors: Louis Chedid, Paris, France; Peter Dukor, Vienna, Austria; Pierre Lefrancier, Gif-sur-Yvette, France; Peter Stütz, Vienna, Austria

[73] Assignee: Sandoz Ltd., Basel, Switzerland

[21] Appl. No.: 544,287

[22] Filed: Jun. 27, 1990

[30] Foreign Application Priority Data

| | | |
|---|---|---|
| Jun. 29, 1989 [DE] | Fed. Rep. of Germany | 3921246 |
| Jun. 29, 1989 [DE] | Fed. Rep. of Germany | 3921248 |
| Jul. 27, 1989 [DE] | Fed. Rep. of Germany | 3924874 |
| Jul. 27, 1989 [DE] | Fed. Rep. of Germany | 3924875 |

[51] Int. Cl.$^5$ ............... A61K 37/02; C07K 9/00
[52] U.S. Cl. ................................ 514/8; 514/18; 530/322; 530/331; 536/53
[58] Field of Search ............ 530/322, 331; 514/8, 514/18; 424/400; 536/53

[56] References Cited

U.S. PATENT DOCUMENTS

| | | | |
|---|---|---|---|
| 4,235,871 | 11/1980 | Papahadjopoulos et al. | 424/89 |
| 4,315,913 | 2/1982 | Durette | 530/322 |
| 4,396,607 | 8/1983 | Lefrancier et al. | 530/322 |
| 4,731,210 | 3/1988 | Weder et al. | 424/450 |
| 4,897,308 | 1/1990 | Vanderberghe et al. | 424/450 |
| 4,939,122 | 7/1990 | Phillips et al. | 514/8 |

FOREIGN PATENT DOCUMENTS 58-172399 10/1983 Japan.
60-078997 5/1985 Japan.

OTHER PUBLICATIONS

Mehta et al., "Uptake of Liposomes and Liposome Encapsulated Muramyl Dipeptide by Human Peripheral Blood Monocytes", RES: Journal of Reticuloendothelial Society 32:155–164 (1982).

Phillips et al., "Anti Infectious Activity of Liposomal MDP", Infection & Immunity Jun. 1987, pp. 1426–1430.

Primary Examiner—Lester L. Lee
Attorney, Agent, or Firm—Robert S. Honor; Melvyn M. Kassenoff; Thomas O. McGovern

[57] ABSTRACT

The 3-O-[N-acetylmuramyl-D-isoglutaminyl]-1,2-di-O-palmitoyl-sn-glycerol derivative of formula I

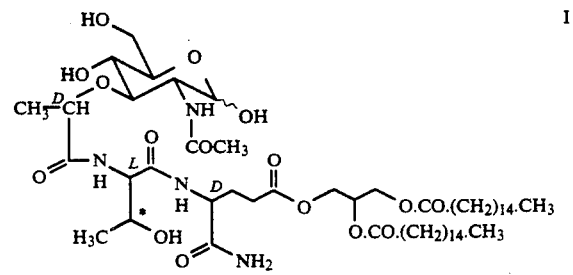

wherein the carbon atom marked with an asterisk * has the R or, respectively, the S configuration, possesses interesting pharmacological, in particular immunomodulating properties. It is particularly useful as an immunomodulant, as an adjuvant in vaccines and as a suppressing agent for IgE formation in e.g. type I allergies and atopical dermatitises.

It is obtained by deprotection of a corresponding compound having one or more hydroxy group(s) in protected form.

7 Claims, 1 Drawing Sheet

Figure
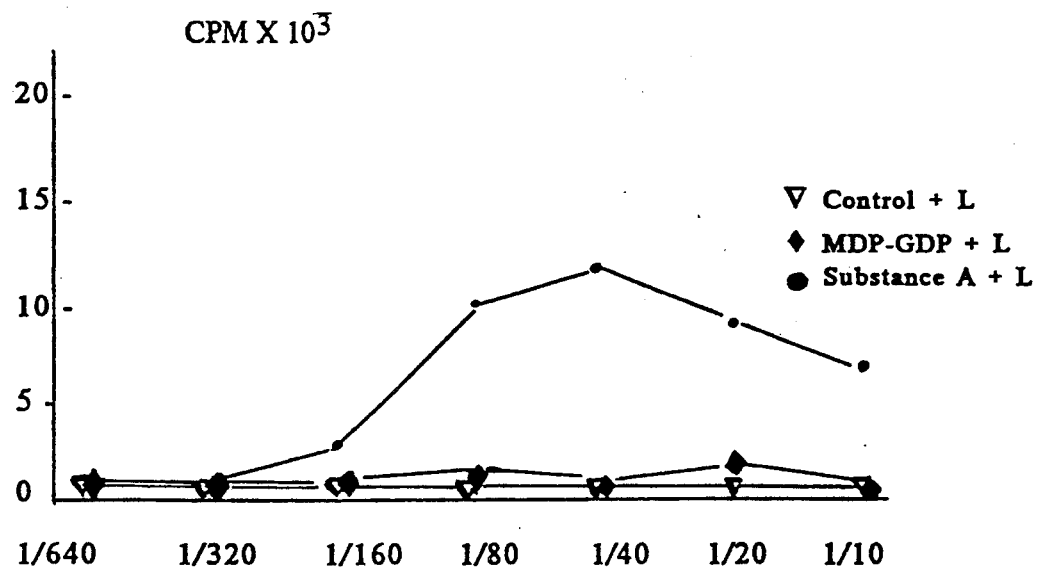
DILUTIONS
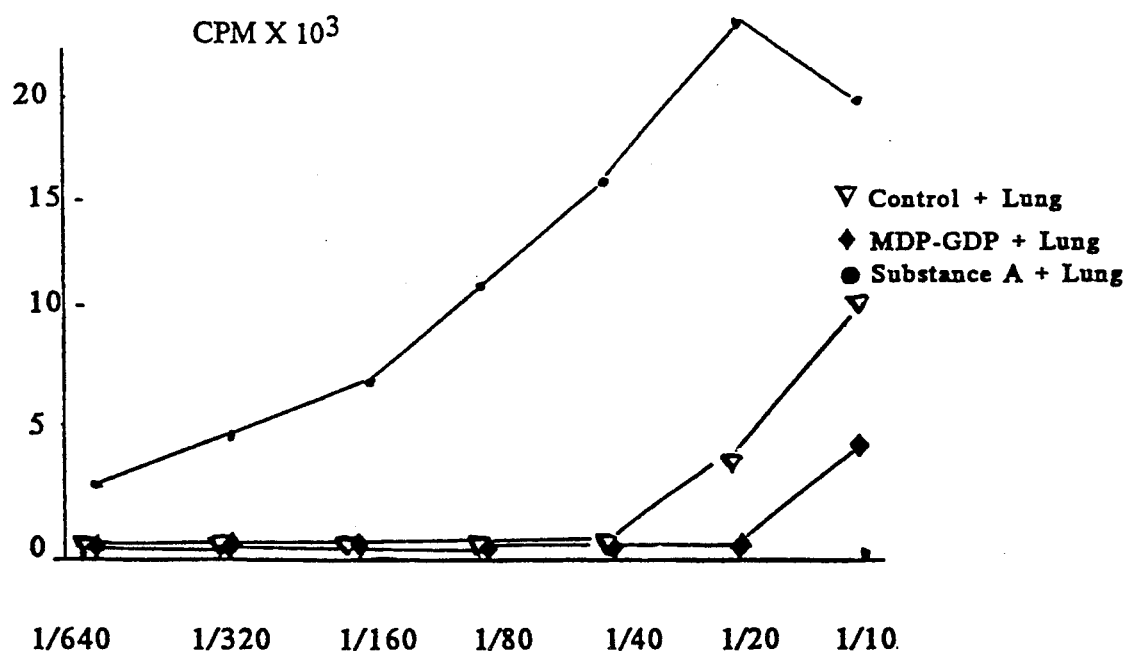
DILUTIONS

MURAMYL DIPEPTIDE DERIVATIVES

The invention concerns the forms of the 3-O-[N-acetylmuramyl-D-isoglutaminyl]-1,2-di-O-palmitoyl-sn-glycerol derivative of formula I

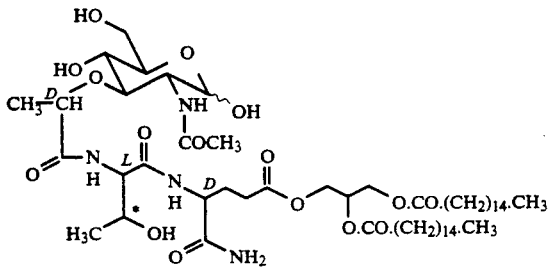

wherein the carbon atom marked with an asterisk * (hereinafter referred to briefly as "the C*") has the R or, respectively, the S configuration. This derivative is hereinafter referred to briefly as "the compound of the invention".

When the C* has the R configuration the corresponding amino acid residue is L-threonyl; when it has the S configuration it is L-allothreonyl. Preferred is the form of the compound of the invention wherein the C* has the R configuration. As appears from the above formula the compound has two anomeric forms.

Compounds with a similar structure and related activity are known from e.g. ANVAR EP 165123; the formula on page 4 therein encompasses the compound of the present invention. The compound of the present invention is, however, nowhere specifically disclosed nor suggested in the above art. It possesses vastly more beneficial properties than the art compounds.

The compound of the present invention may also be named L-threonyl-MDP-GDP and, respectively, L-allothreonyl-MDP-GDP.

The present invention further comprises a process for the preparation of the compound of formula I comprising deprotecting a corresponding compound of formula II

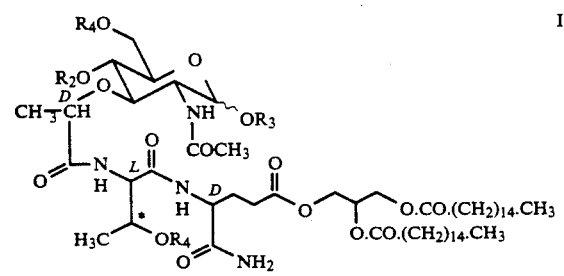

wherein the C* is as defined above and $R_1$ to $R_4$ independently are a hydroxy-protecting group.

The process of the invention may be effected in conventional manner for splitting off hydroxy-protecting groups. The starting material may be the α- or β-glycoside anomer or a mixture thereof. Deprotection may be effected in one or in several reaction steps. The compound of formula I is normally obtained as a mixture of both anomeric forms. These may be separated, if desired, by conventional methods. The process may e.g. be effected reductively, preferably with hydrogen in a palladium catalyst on charcoal, using e.g. acetic acid as solvent. Any conventional hydroxy-protecting group susceptible of hydrogenation may be used, e.g. benzyloxycarbonyl or benzyl. $R_1$ and $R_2$ may also form together a common protecting group such as benzylidene. Deprotection may also be effected e.g. under acidic conditions. A preferred protecting group for deprotection under acidic conditions is tert-butoxycarbonyl (BOC).

The starting materials may also be prepared in conventional manner, e.g. according to the following reaction scheme:

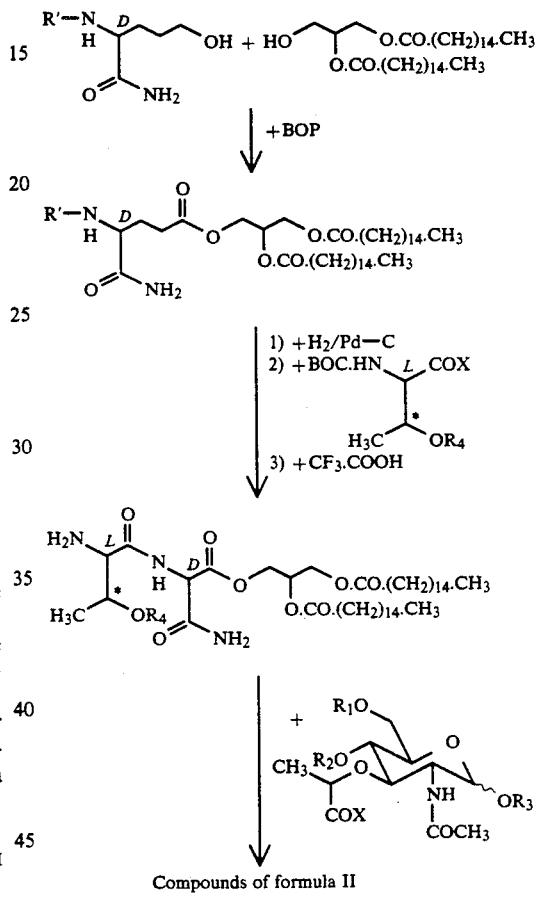

Compounds of formula II

In the above scheme the C* and $R_1$ to $R_4$ are as defined above and

R' is an amino-protecting group,

X is an activated carboxylic acid form,

BOP is a group benztriazol-1-yloxytris-(dimethylamino)phosphonium hexafluorophosphate and BOC is tert-butoxycarbonyl.

Splitting off of R' preferably is effected under acidic conditions. R' preferably is benzyloxycarbonyl. X preferably is —OC(=O)—Oalkyl, such as —OC(=O)—OCH$_2$CH(CH$_3$)$_2$.

The following Examples illustrate the invention. All temperatures are in degrees Centigrade. The abbreviations used have the following meaning:

BOC = tert-butoxycarbonyl
Bzl = benzyl
alloThr = L-allothreonyl
Thr = L-threonyl
Z-D-iGln = carbobenzoxy-D-isoglutamine
Pd/C = palladium on charcoal tBDMS = tert-butyldimethylsilyl

EXAMPLE 1

3-O-[N-Acetylmuramyl-L-threonyl-D-isoglutaminyl]-1,2-di-O-palmitoyl-sn-glycerol (C* has the R configuration)

120 mg 3-O-[1-α-O-benzyl-4,6-O-benzyliden-N-acetylmuramyl-O-benzyl-L-threonyl-D-isoglutaminyl]-1,2-di-O-palmitoyl-sn-glycerol are dissolved in 20 ml of 100% acetic acid and reacted with prehydrogenated catalyst [90 mg 10% Pd/C, 15 mg palladium chloride ($PdCl_2$) in 20 ml of acetic acid 100%, hydrogenated for 45 minutes with hydrogen]. The mixture is stirred for 2 hours under hydrogen, the catalyst is filtered off, the solution concentrated and evaporated to dryness thrice with toluene. The residue is chromatographed over silicagel using dichloromethane/methanol/diisopropylether 4:1:1 as the eluant. The resultant product is chromatographed over Sephadex LH-20 using dichloromethane/methanol 1:1 as the eluant. The solution is evaporated to dryness and lyophilised from acetic acid. The title compound (mixture of both anomers) is obtained:

$^1$H-NMR: 0.90(t,J=7,6H); 1.22(d,J=7,3H); 1.25(s,48H); 1,41(d,J=7,3H); 1.64(m,4H); 2.00(m,3H); 2.22(m,1H); 2.34(m,4H); 2.48(m,2H); 3.40–3.98(m,6H); 4.12–4.60(m,8H); 5.20(d,J=3,1H); 5.26(m,1H).

The starting material is obtained as follows:

a) 740 mg Z-D-iGln are dissolved into 6 ml of a mixture of dry dimethylformamide/tetrahydrofurane 1:1 and reacted in darkness with 1.46 g benztriazol-1-yloxytris-(dimethylamino)phosphonium hexafluorophosphate and 365 µl of N-methylmorpholine. After 30 minutes 1.14 g 1,2-dipalmitoyl-sn-glycerol and 270 mg imidazole are added and the reaction mixture is stirred further in darkness for 4 days. After evaporation of the solvent mixture the residue is chromatographed over silicagel using dichloromethane/methanol 20:1 as the eluant. 3-O-[Benzyloxycarbonyl-D-isoglutaminyl]-1,2-di-O-palmitoyl-sn-glycerol is obtained:

$^1$H-NMR: 0.89(t,J=7,6H); 1.28(s,48H); 1.62(m,4H); 1.95(m,1H); 2.15(m,1H); 2.34(m,4H); 2.46(m,2H); 4.25(m,5H); 5.12(s,2H); 5.27(m,1H); 7.35(s,5H).

b) 400 mg of the compound obtained under a) above are dissolved in 20 ml of 100% acetic acid and reacted with 40 mg Pd/C 10%. Stirring is pursued for 2 hours under a hydrogen atmosphere, the catalyst is filtered off and the residue evaporated thrice to dryness with toluene. The residue is dissolved in 8 ml of dichloromethane under addition of 60 µl of N-methylmorpholine (=solution A).

160 mg BOC-Thr(Bzl)-OH are dissolved in 8 ml of dichloromethane together with 233 µl of N-methylmorpholine and 73 µl of chloroformic acid isobutylester and the mixture is stirred at room temperature for 45 minutes (=solution B).

Solution B is cooled to +4° and solution A is added thereto. The mixture is stirred for 18 hours at room temperature, the solvent is evaporated and purification effected by chromatography over silicagel using dichloromethane/methanol 100:1 to 100:3 as the eluant;

3-O-[tert-butoxycarbonyl-O-benzyl-L-threonyl-D-isoglutaminyl]-1,2-di-O-palmitoyl-sn-glycerol is obtained:

$^1$H-NMR: 0.88(t,J=7,6H); 1.26(s,48H); 1.47(s,9H); 1.60(m,4H); 1.94(m,1H); 2.14–2.58(m,7H); 4.10–4.34(m,6H); 4.45(m,2H); 4.60(d,2H); 5.15(m,1H); 5.23(m,1H); 5.40(m,1H); 6.35(m,1H); 7.13(m,1H); 7.30(m,5H).

c) 580 mg of the compound obtained under b) above are reacted at +4° with 20 ml of trifluoroacetic acid and the mixture is stirred for 30 minutes. The solution is concentrated and evaporated to dryness twice with toluene. The residue is reacted with 10 ml of dichloromethane and 65 µl of N-methylmorpholine (=solution A).

278 mg α-O-benzyl-4,6-benzylidene-N-acetylmuramic acid are dissolved in 10 ml of dichloromethane together with 259 µl of N-methylmorpholine and 81 µl of chloroformic acid isobutylester and the mixture is stirred for 35 minutes at room temperature (=solution B).

Solution A is added dropwise to solution B at +4° and the mixture is allowed to stand for 2 days at room temperature. After evaporation of the solvent the residue is chromatographed over silicagel using dichloromethane/methanol from 100:1 to 10:1 as the eluant. 3-O-[1-α-O-Benzyl-4,6-O-benzylidene-N-acetylmuramyl-O-benzyl-L-threonyl-D-isoglutaminyl]-1,2-di-O-palmitoyl-sn-glycerol is obtained:

$^1$H-NMR: 0.88(t,J=7,6H); 1.22(d,J=7,3H); 1.37(d,J=7,3H); 1.60(m,4H); 1.98(s,3H); 2.02(m,1H); 2.30(m,4H); 2.44(m,4H); 3.66–3.94(m,4H); 4.06–4.46(m,10H); 4.90(d,J=4,1H); 5.25(m,1H); 5.60(s,1H); 6.78(d,1H); 7.10(d,1H); 7.40(m,10H); 7.60(d,1H).

EXAMPLE 2

3-O-[N-Acetylmuramyl-L-allothreonyl-D-isoglutaminyl]-1,2-di-O-palmitoyl-sn-glycerol C* has the S configuration The title compound is obtained in a manner analogous to Example 1, starting from the corresponding L-allothreonyl compound:

$^1$H-NMR: 0.88(t,J=7,6H); 1.25(s,48H); 1.40(d,J=7,3H); 1.64(m,4H); 2.00(m,3H); 2.24(m,1H); 2.35(m,4H); 2.48(m,2H); 3.40–3.98(m,6H); 4.10–4.60(m,8H); 5.23(d,J=3,1H); 5.26(m,1H).

The L-allothreonyl compound used as a starting material is obtained as follows:

a) 3-O-[Benzyloxycarbonyl-D-isoglutaminyl]-1,2-di-O-palmitoyl-sn-glycerol is prepared as described in Example 1, step a);

b) 3-O-[Benzyloxycarbonyl-O-tert-butyldimethylsilyl-L-allothreonyl-D-isoglutaminyl]-1,2-di-O-palmitoyl-sn-glycerol is prepared in a manner analogous to Example 1, step b), using Bzl-alloThr(tBDMS)-OH in place of BOC-Thr(Bzl)-OH:

$^1$H-NMR: 0.02(s,3H); 0.04(s,3H); 0.93(m,15H); 1.16(d,J=7,3H); 1.25(m,48H); 1.67(m,4H); 1.90(m,1H); 2.07(m,1H); 2.28(m,4H); 2.42(m,2H); 4.03–4.40(m,7H); 5.08(m,2H); 5.13(m,1H); 7.30(m,5H); 7.46(d,1H);

c) 3-O-[1-α-O-Benzyl-4,6-O-benzylidene-N-acetylmuramyl-O-tert-butyldimethylsilyl-L-allothreonyl-D-isoglutaminyl]-1,2-di-O-palmitoyl-sn-glycerol is prepared in a manner analogous to Example 1, step c):

$^1$H-NMR: 0.08(s,3H); 0.10(s,3H); 0.88(m,15H); 1.17(d,J=7,3H); 1.25(m,48H); 1.37(d,J=7,3H); 1.64(m,4H); 1.95(m,1H); 1.97(s,3H); 2.13(m,1H); 2.34(m,4H); 2.46(m,2H); 3.65(m,4H); 3.98–4.40(m,10H); 4.66(dd,J=13.40,1H); 5.15(d,J=3,1H); 5.25(m,1H); 5.60(s,1H); 7.25–7.53(m,10H); 8.23(d,1H).

The compound of the invention possesses excellent pharmacological acticity. It is therefore useful as a pharmaceutical.

In particular it has been found to have a pronounced immunomodulating activity. This activity can be demonstrated using various test methods explained in more detail hereinafter.

The abbreviations used have the following meaning:
Substance A: compound form of Example 1:
Substance B: compound form of Example 2;
ABC: hapten-specific antibody-building cells;
BPO-BSA: benzylpenicilloyl-bovine serum albumin;
BPO-KLH: benzylpenicilloyl-keyhole limpet hemocyanin;
BSA: bovine serum albumin;
CMI: cell-mediated immunity;
ConA: Concanavalin-A;
CSF: colony-stimulating factor;
CY: cyclophosphamide;
DTH: delayed-type hypersensitivity;
ELISA: enzyme-linked immunosorbent assay;
FIA: Freund's incomplete adjuvant;
HI: humoral immunity;
IFN-γ: interferon gamma;
IL-1(IL-1β): interleukin-1 (interleukin-1β);
LAF: lymphocyte-activating factor;
LPS: lipopolysaccharide;
MDP: muramyl dipeptide;
MDP-GDP: 3-O-[N-acetylmuramyl-L-alanyl-D-isoglutaminyl]-1,2-di-O-palmitoyl-sn-glycerol (compound of Example 1 in ANVAR EP 165123);
NBT: Nitro Blue Tetrazolium;
PBL: peripheral blood leukocytes;
PEC: peritoneal excsudate cells;
PHA: phytohaemagglutinin;
PMA: phorbol myristate acetate;
PMN: polymorphonuclear cells;
TNF: tumor necrosis factor;

A) It has been found that the compound of the invention is characterized by much less side effects as compared to structurally similar compounds such as MDP-GDP; it is therefore better tolerated. This particularly beneficial property can be evidenced e.g. in the following assays:

1) Pyrogenicity in the rabbit: the test method is as described in the literature, e.g. in the U.S. Pharmacopeia. The results obtained are as follows (Table 1):

TABLE 1

| | Pyrogenicity in the rabbit | |
|---|---|---|
| Substance | Highest non-pyrogenic dose (μg/kg i.v.) | Lowest pyrogenic dose (μg/kg i.v.) |
| A | 1000 | 5000 |
| B | 20 | 50 |
| MDG-GDP | 10 | 20 |

2) Toxic synergism with LPS: in this assay Swiss mice receive intravenously LPS and either MDP-GDP or substance A at the dosages indicated (Table 1bis):

TABLE 1bis

| | Absence of toxic synergism with LPS | |
|---|---|---|
| Substance | Treatment | Cumulative mortality (dead/total) |
| Control | + LPS 25 μg | 0/18 |
| MDP-GDP (300 μg) | + LPS 25 μg | 17/18 |
| A (300 μg) | + LPS 25 μg | 3/18 |

All mice received 25 μg of *S. enteridis* LPS i.v. alone or with either MDP-GDP or substance A. Results were obtained in 3 identical assays using 6 mice/group.

The results obtained in the above two assays (pyrogenicity and toxic synergism, Tables 1 and 1bis) show a marked improvement in side effects as compared with MDP-GDP.

Further test methods are e.g. as follows:

a) TNF-induction in mouse bone marrow cultures, in rabbit PBLs (without preactivation with IFN-γ) and in human PBLs:

This assay is described in detail in T. J. Sayers et al., *J. Immunol.* 136 (1986) 2935-2940. TNF activity is measured from the lytic activity on L 929 cells. The results are summarized in Table 2 and show that both forms A and B of the compound of the invention are very weak inductors of TNF and thus possess a markedly lower endotoxic potential than the reference compounds. These results fit also well with the results obtained for substance A using peripheral human or rabbit mononuclear blood cells isolated with Ficoll (Tables 3 and 4):

TABLE 2

| TNF induction in murine bone marrow and macrophage cultures | | | |
|---|---|---|---|
| | Concentration | TNF (international units IU) | |
| Substance | (μg/ml) | no INF-γ | INF-γ (100 IU) |
| A | 1 | <5 | <5 |
| | 10 | <5 | 25 |
| B | 1 | <5 | 99 |
| | 10 | <5 | 40 |
| MDP-GDP | 1 | <5 | 205 |
| | 10 | <5 | 276 |
| LPS | 0.01 | 377 | 2.245 |
| Salmonella abort. equi | 0.001 | 17 | 119 |
| Solvent alone | — | <5 | <5 |

TABLE 3

| TNF induction in rabbit peripheral mononuclear blood cells (without preactivation with IFN-γ) | | | | | |
|---|---|---|---|---|---|
| | Concen- tration | TNF (intenational units IU) | | | |
| | | First experiment | | Second experiment | |
| Substance | (μg/ml) | Rabbit 1 | Rabbit 2 | Rabbit 3 | Rabbit 4 |
| A | 1 | <8 | <8 | 39 | 28 |
| | 10 | 44 | 76 | 204 | 163 |
| MDP-GDP | 1 | 233 | 328 | 196 | 157 |
| | 10 | 571 | 687 | 643 | 724 |
| LPS | 0.01 | 989 | 1198 | 1002 | 637 |
| Salmonell abort. equi | 0.001 | 361 | 680 | 318 | 230 |
| Solvent alone | — | <8 | <8 | 14 | 20 |
| Medium alone | — | <8 | <8 | 27 | 26 |

TABLE 4

| TNF induction in peripheral human mononuclear blood cells | | | |
|---|---|---|---|
| | Concen- tration | TNF (pg/ml) First experiment Second experiment | |
| Substance | (μg/ml) | Donor 1 Donor 2 | Donor 3 |
| A | 1 | 27    82 | 63 |
| | 10 | 248    196 | 163 |
| | 20 | 291    225 | 198 |
| MDP-GDP | 1 | 493    107 | — |

TABLE 4-continued

| | | TNF induction in peripheral human mononuclear blood cells | | |
|---|---|---|---|---|
| | Concentration | TNF (pg/ml) First experiment Second experiment | | |
| Substance | (μg/ml) | Donor 1 | Donor 2 | Donor 3 |
| | 10 | 654 | 94 | 59 |
| LPS | 0.01 | 26 | 1000 | 538 |
| Salmonella abort. equi | 0.001 | 18 | 1195 | 699 |
| Solvent alone | — | 0 | 0 | 0 |
| Growth medium alone | — | 0 | 0 | 0 | b) Induction of IL-1:

The activity of IL-1β or, respectively, LAF is assayed according to the methods of J. Gery et al., *J. Exp. Med.* 136 (1972) 128–142 and J. Oppenheim et al., *Cellular Immunol.* 50 (1980) 71–81. The results (Table 5) indicate that proliferation is significantly increased only at the highest concentration of 50 μg/ml as compared to solvent alone:

TABLE 5

| | Induction of LAF activity (IL-1β) in murine elicited peritoneal macrophages | | |
|---|---|---|---|
| | Concentration | Activity (cpm) | |
| Substance | (μg/ml) | Dilution 1:4 | Dilution 1:8 |
| A | 1 | 446 | 361 |
| | 10 | 1014 | 1267 |
| | 50 | 2338 | 2701 |
| MDP-GDP | 1 | 691 | 391 |
| | 10 | 1220 | 380 |
| | 50 | 4491 | 1106 |
| LPS | 10 | 5809 | 3096 |
| Salmonella abort. equi | 1 | 329 | 326 |
| Growth medium alone | — | 427 | — |
| Supernatant alone | — | 374 | 513 |
| Solvent alone | 10% | 1546 | 1645 | c) Induction of macrophage toxicity (mouse PECs) against tumor cells (P 815):

Mice are pretreated i.p. with 15 ml of 2.9% thioglycolate bouillon (Merck-Darmstadt, FRG). After 4 days macrophages are exsudated into the peritoneal cavity and harvested by lavage. When these elicited, adherent mouse macrophages are cocultivated with tumor cells, LPS or immunostimulatory substances they can activate the macrophages, with resultant lysis or growth inhibition of the tumor cells. This activation can be further enhanced by addition of IFN-γ. The number of surviving cells after 24 hours of cultivation is determined by measurement of [³H]-thymidine incorporation. Comparison with a negative control and a LPS positive control gives a measurement of lytic or cytotoxic activity in % for a given concentration of test substance (Table 6):

TABLE 6

| | Induction of macrophage cytotoxicity against tumor cells | | | |
|---|---|---|---|---|
| | Concentration | % inhibition of P 815 tumor cells | | |
| Substance | (μg/ml) | no IFN-γ | IFN-γ (1 U) | IFN-γ (5 U) |
| A | 1 | 55 | 41 | 94 |
| | 10 | 62 | 28 | 99 |
| MDP-GDP | 1 | 71 | 40 | 99 |
| | 10 | 62 | 62 | 99 |
| LPS | 0.01 | 77 | 98 | 99 |
| Salmonella abort. equi | 0.001 | 84 | 60 | 99 |
| Solvent alone | — | 5 | 10 | 10 |
| Growth medium alone | — | 0 | 10 | 10 | d) Induction of LAF activity in mice PECs after incubation for 24 hours (thymocytes assay, costimulation with PHA 1:50):

In this assay (*J. Exp. Med.* 136 [1972] 128–155) substances A and B exhibit a profile of activity similar to that of MDP-GDP.

e) A further activity of great significance in tumor therapy which has been found to be possessed by the compound of the invention using rodents pretreated with cyclophosphamide or with X-rays irradiation is a dose-dependent stimulation of proliferation and differentiation of myeloblasts into mature lymphocytes in bone marrow.

f) Proliferative response of bone-marrow cells from mice treated with cyclophosphamide: mice received i.p. 5 mg of cyclophosphamide one day after a treatment with MDP-GDP or substance A. Cells were harvested on day 4 of the cyclophophamide treatment and incubated in the presence of conditioned medium either from L929 cells ("L") containing CSF-1 (E. R. Stanley and L. G. Guilbert, *J. Immunol. Methods* 42 [1981] 253, or from lungs from LPS-treated mice ("lung" GM-CSF) as described by Sheridan and Metcalf, *J. Cell Physiology* 81 [1973] 11, at various dilutions. The response of cells to CSF or GM-CSF is measured by ³H-thymidine incorporation as compared with controls. Results show that in contrast to MDP-GDP substance A can restore the proliferative response of cells to a CSF treatment (see the Figure):

Explanation of the Figure: Proliferative response of bone marrow cells from mice treated with CY on day 0 and MDP-GDP (300 μg) or substance A (300 μg) on day -1

▽: control + L cells containing CSF or, respectively, control + lung GM-CSF;

◆: MDP-GDP + L cells containing CSF or, respectively, MDP-GDP + lung GM-CSF;

●: substance A + L cells containing CSF or, respectively, substance A + lung GM-CSF.

g) Enhancement of non-specific resistance of mice to infection: The capacity of substance A to increase the resistance of mice to infection has been evaluated in mice in a model of bacterial infection. Swiss mice are treated intravenously with MDP-GDP or substance A. After 24 hours they receive a lethal challenge ($8 \times 10^4$ organisms) of Klebsiella pneumoniae (Table 7):

TABLE 7

| | Protection against Klebsiella infection in mice | | |
|---|---|---|---|
| | Treatment (i.v. on day -1) | | |
| Substance | (μg/mouse) | Survival | |
| None | — | 1/32 | |
| MDP-GDP | 30 | 14/24 | (p < 0.01) |
| | 100 | 19/24 | (p < 0.01) |
| A | 30 | 10/24 | (p < 0.01) |
| | 100 | 14/24 | (p < 0.01) |

Swiss mice are administered on day -1 the compounds by the intravenous route. They are challenged by the same route with $8 \times 10^4$ bacteria. Deaths are recorded for three weeks after the challenge.

It can be seen from Table 7 that as compared to their untreated controls MDP-GDP and substance A dramatically increase the non-specific resistance of mice to infection.

h) Adjuvant activity: The capacity of substance A to induce a cell-mediated and increase the humoral specific responses to an antigen has been evaluated. Control and experimental Hartley male guinea pigs weighing 300 g received in the hind foot pads a total dose of 1 mg of ovalbumin in 0.2 ml of a water-in-oil emulsion (Freund's incomplete adjuvant, FIA). For experimental groups the adjuvant was added at a dosage of 0.1 mg to the emulsion.

In order to evaluate their cell-mediated immunity (CMI) animals were skin-tested on day 21 with an intradermal injection of 0.1 mg of ovalbumin in saline. Dermal reactions were checked after 6, 24 and 48 hours and results are expressed as diameters of induration after 48 hours. In order to evaluate their humoral immunity (HI) animals were bled by heart puncture on day 24. Anti-ovalbumin antibody titers were measured by ELISA under standard conditions. Individual titers and means are given. It is shown in Table 8 that substance A stimulates even more than MDP-GDP both CMI and HI specific responses:

TABLE 8

Adjuvant activity on the humoral and cell-mediated immune responses

| Substance | DTH[1] (diameters) (mm of induration) | Humoral response[2] (ELISA titers) |
|---|---|---|
| Controls | 0 (6) | 8000 - 21000 - 21500 - 37000 - 65000 - 95000 - (41250) |
| MDP-GDP | 8 - 14 - 15 - 17 (13.5) | 247000 - 295000 - 641000 - 325000 (377000) |
| A | 15 - 15 - 18 - 20 - 20 - 25 (18.5) | 100000 - 172000 - 780000 - 850000 - 472000 - 330000 - (450000) |

[1]Results are expressed as diameters of induration after 48 hours. Individual measurements and arithmetical means (between brackets) are given.
[2]Anti-ovalbumin antibody titers were measured by ELISA under standard conditions. Individual titers and means are given.

i) Influence on the response of rabbit peripheral blood lymphocytes to mitogens:

Substance A has been injected intravenously to rabbits at a dose of 100 μg. Before and three hours after this administration samples of blood were collected. Lymphoblastic transformation assays were performed using mononuclear cells which were incubated with ConA or PHA. The mitogenic effect was measured by the increase in $^3$H-thymidine incorporation and is expressed as number of counts per minute (cpm). Results are reported in Table 9:

TABLE 9

Lymphoblastic transformation by mitogens in vitro after in vivo treatment with substance A

| | | In vivo incubation with: | | | |
|---|---|---|---|---|---|
| | | ConA | | PHA | |
| Rabbits | Saline | (1 μg/ml) | (10 μg/ml) | (1 μg/ml) | (10 μg/ml) |
| Control 1 T0 | 1086 | 3782 | 6190 | 3078 | 2423 |
| T3 | 1612 | 5570 | 6844 | 6880 | 5905 |
| Control 2 T0 | 577 | 3354 | 2459 | 3316 | 1610 |
| T3 | 383 | 5194 | 428 | 2095 | 1206 |
| A T0 | 2926 | 3132 | 5204 | 2479 | 2591 |
| treatd 1 T3 | 983 | 22241 | 39469 | 16754 | 30270 |
| A T0 | 412 | 6342 | 2778 | 10149 | 2936 |
| treated 2 T3 | 324 | 10721 | 118597 | 15734 | 91434 |
| A T0 | 487 | 15521 | 6917 | 10020 | 12482 |
| treated 3 T3 | 239 | 55690 | 50572 | 32228 | 37538 |
| A T0 | 732 | 951 | 1287 | 600 | 569 |
| T3 | 1327 | 9252 | 6493 | 4570 | 2648 |

It can be seen from Table 9 that as compared with cells of non-treated rabbits the in vivo treatment with substance A has significantly increased the capacity of lymphocytes to respond in vitro to suboptimal dosages of nitrogen.

j) Response of blood polymorphonuclear (PMN) cells after in vitro or in vivo treatment:

Oxidative response and candidacidal potency were evaluated according to classical methods. Purified PMN from human or guinea pig blood were cultured in the presence of substance A before measuring the oxidative burst in response to PMA or C.albicans cells within one hour, or the growth of C.albicans for 18 hours. The results (Table 10) show the stimulating effect of substance A on these cells irrespective of their origin (human or guinea pig):

TABLE 10

Influence of preincubation with Substance A on human or guinea pig PMN responses

| Blood cells | Preincubation[a] with substance A (μg/ml) | Oxidative response[b] to PMA (20 nM) | Yeast cells (ratio 30:1) | Candidacidal potency at ratio 30:1 (PMN:yeast) | 100:1 (PMN:yeast) |
|---|---|---|---|---|---|
| Human PMN | none | 30.3 | 4.2 | 2.5 | 58.1 |
| | 0.1 | — | — | 0 | 47.6 |
| | 1 | — | — | 3.3 | 75.6 |
| | 10 | 69.2 | 29.7 | 21.2 | 92.9 |
| Guinea pig PMN | none | 42.9 | 18.9 | — | 42.4 |
| | 0.1 | — | — | — | 61.8 |
| | 1 | — | — | — | 84.9 |
| | 10 | 52.6 | 24.3 | — | 93.3 |

[a]Preincubation for 1 hour
[b]Expressed as percentage of NBT reducing cells one hour after addition of PMA or C. albicans cells
[c]Percent inhibition of C. albicans growth measured by the decrease of $^3$H-glucose incorporation in yeast cells k) Ex vivo assays were performed in guinea pigs given substance A by the subcutaneous route (500 μg/kg) 3 or 18 hours before collecting blood by cardiac puncture. The response of purified blood PMN was directly determined in vitro after addition of PMA or C.albicans cells. As shown in Table 11 pretreatment of guinea pigs 18 hours previously induces a stronger response of PMN when exposed subsequently to PMA or C.albicans cells, whereas pretreatment of animals 3 hours before collecting the cells was ineffective:

TABLE 11

Influence of pretreatment with substance A (500 µg/kg) on responsiveness of guinea pig PMN

| Pretreatment | PMA (20 nM) | Oxidative response to yeast cells[a] (ratio 30:1) | Candidacidal potency[b] at ratio 30:1 | 100:1 |
|---|---|---|---|---|
| Saline | 55.8 | 33.3 | 17.2 | 25.6 |
| Substance A (h-3) | 61.1 | 35.2 | 15 | 17.2 |
| Substance A (h-18) | 84.9 | 62.7 | 60.1 | 82.1 |

[a]Expressed as percentage of NBT reducing cells according to E. Pick et al., J. Reticuloendothelial Soc. 30 [1981] 581 one hour afater addition of PMA or *C. albicans* cells at the ratio of 30:1 (PMN:yeast cells)
[b]Percent inhibition of *C. albicans* growth measured by the decrease of $^3$H-glucose incorporation in yeast cells It can thus be concluded on the basis of the test results set out under A) above that overall the compound of the invention possesses much more beneficial pharmacological activity than structurally similar compounds such as MDP-GDP.

The compound of the invention is useful as a modulator of unspecific antimicrobial resistance for systemic enhancement of immune response and unspecific immunity.

It is thus indicated e.g. in the curative treatment or in the supportive treatment (i.e. together with further specific or supportive forms of therapy) of conditions of decreased immune response, in particular conditions of decreased cellular and humoral immune response and conditions of decreased oversensitivity reactions of the delayed type, and further in the treatment of conditions generally in which a modulation of the immune response is desired.

It is in particular useful in the curative or supportive treatment of pathological conditions related to idiopathic immunodeficiencies or immunodeficiencies of the type encountered in geriatric patients or in patients with heavy burns or generalised infections.

It is further useful in the curative or supportive treatment of viral infections such as disseminated Herpes and disseminated varicella infections and Morbus Hodgkin and further malignant tumors.

For the above indications the dosage to be used will depend of course on the nature and severity of the disease to be treated, the mode of administration and the compound form used. For the large subject a suitable parenteral dosage is from about 0.1 mg to about 70 mg, administered e.g. once for the achievement of an adjuvant effect, e.g. in supportive treatment, or daily. Repeated administration may conveniently be effected two to four times per day or in retard form. Indicated unit dosage forms include from about 0.025 mg to about 35 mg of compound of the invention in situations of repeated administration and up to about 70 mg when a single administration for adjuvant treatment is desired.

B) Its immunomodulating activity further makes the compound of the invention useful as an adjuvant in vaccines. For this mode of utilization the indicated daily dosage is from about 0.1 mg to about 50 mg, preferably from about 0.5 mg to about 10 mg, especially about 7 mg, administered on the day of vaccination. Conveniently a second administration at the same dosage is effected 2 to 4 weeks thereafter.

C) It has further been found that the compound of the invention modifies the hapten-specific immunoglobulin isotype response in mice. This activity is evidenced with an assay for the determination of the amount of hapten-specific antibody-forming cells (ABCs). The immunization scheme is as follows: Balb/c mice receive an intraperitoneal injection of 10 µg BPO-KLH in 0.2 ml of aluminum hydroxide gel at days 0, 21 and 42. The mice are then separated into two groups: the first group is given 10 µg/mouse of compound of the invention (substance A) p.o. on days 44 and 45, the second (control) group receives saline. The animals are sacrificed on days 46, 51 and 70 and lymphocytes extracted from their Peyer plaques, mesenteric lymph nodes and spleen. The cells from 6 mice are pooled and the number of ABCs ex vivo determined in an Elispot assay using plaques layered with BPO-BSA. The results obtained are indicated in Table 12:

TABLE 12

Hapten-specific immunoglobulin isotype response in mice

| Day of sacrifice | Organ | Hapten-specific antibody-forming cells (ABCs/$10^7$ cells) | | | | | | | |
|---|---|---|---|---|---|---|---|---|---|
| | | IgM | | IgG | | IgE | | IgA | |
| | | Co | A | Co | A | Co | A | Co | A |
| 46 | PP | <1 | <1 | <1 | <1 | <1 | <1 | <1 | <1 |
| | ML | 211 | 218 | 181 | 315 | 315 | <1 | 104 | 89 |
| | SP | 303 | 410 | 395 | 485 | 288 | <1 | 143 | 123 |
| 51 | PP | <1 | <1 | <1 | <1 | <1 | <1 | <1 | <1 |
| | ML | 197 | 320 | 273 | 362 | 286 | 5 | 98 | 111 |
| | SP | 630 | 795 | 718 | 812 | 193 | 15 | 77 | 94 |
| 70 | PP | <1 | <1 | <1 | <1 | <1 | <1 | <1 | <1 |
| | ML | 187 | 174 | 235 | 347 | 133 | 111 | 62 | 53 |
| | SP | 1316 | 918 | 943 | 1012 | 188 | 164 | 84 | 77 |

PP = Peyer plaques;
ML = mesenteric lymph nodes;
SP = spleen;
CO = contorl (physiological saline)

The above results show that following immunization of the mice in the indicated manner ABCs of all Ig isotype classes could be found in the mesenteric lymph nodes and in the spleen. The number of IgM- and IgG-forming cells was clearly larger in spleen cells than in mesenteric lymph node cells, while roughly similar numbers were found in both organs as regards IgA and IgE ABCs. A treatment with the compound of the invention (substance A) according to the above scheme resulted in both organs in increased IgG ABCs content, whereas the number of IgE-forming ABCs was reduced. The effect appears to be transient.

On day 46 no IgE-forming ABCs could be found in any of the two organs, on day 51 the content was still very low. On day 70 no difference with the controls could be determined.

This is indicative of a regulatory function of the compound of the invention in allergic diseases.

When the above assay is repeated as described above but with administration of test substance on day 44 and sacrifice of the animals on days 45, 46, 58 and 70 the following results are obtained (Table 13):

TABLE 13

Decrease in IgE-forming ABCs in mouse spleen

| Day of sacrifice | Test dosage (Substance A, mg/kg) | Number of | | | |
|---|---|---|---|---|---|
| | | IgE-forming ABCs | | IgA-forming ABCs | |
| | | (per $10^7$ cells) | | | |
| | | Trial 1 | Trial 2 | Trial 1 | Trial 2 |
| 45 | none | 317 | 239 | 139 | 131 |
| | 0.1 | 251 | 215 | 207 | 93 |
| | 1 | 264 | 231 | 66 | 111 |
| | 10 | 270 | 201 | 170 | 106 |
| | 100 | 253 | 216 | 202 | 119 |
| 46 | none | 313 | 291 | 156 | 166 |
| | 0.1 | 177 | 115 | 103 | 191 |
| | 1 | 70 | 94 | 158 | 202 |
| | 10 | 82 | 64 | 217 | 289 |

TABLE 13-continued

| | | Decrease in IgE-forming ABCs in mouse spleen | | | |
|---|---|---|---|---|---|
| | | Number of | | | |
| | Test dosage | IgE-forming ABCs | | IgA-forming ABCs | |
| Day of sacrifice | (Substance A, mg/kg) | (per $10^7$ cells) | | | |
| | | Trial 1 | Trial 2 | Trial 1 | Trial 2 |
| | 100 | 54 | 72 | 140 | 218 |
| 58 | none | 277 | 189 | 93 | 56 |
| | 0.1 | 201 | 152 | 88 | 76 |
| | 1 | 196 | 155 | 73 | 90 |
| | 10 | 138 | 119 | 61 | 81 |
| | 100 | 56 | 64 | 78 | 43 |
| 70 | none | 166 | 108 | 34 | 112 |
| | 0.1 | 136 | 95 | 122 | 74 |
| | 1 | 144 | 92 | 99 | 85 |
| | 10 | 153 | 121 | 130 | 105 |
| | 100 | 129 | 113 | 108 | 101 |

In view of the above activity the compound of the invention is further useful as IgE formation suppressing agent, particularly for the treatment of type-I allergies and atopical dermatitises.

For these indications the indicated daily parenteral dosage is from about 3 μg/kg to about 20 μg/kg, conveniently administered two to four times a day or, preferably, in retard form at intervalls of two or more days. Unit dosage forms contain from about 2 mg to about 15 mg. The total daily dosage is from about 4 mg to about 60 mg.

D) Further, it has been found in the CSF-induction assay in mice by simultaneous administration of substance A and LPS that in contrast to MDP-GDP the compound of the invention exerts a certain degree of synergistic activity with LPS.

Preferred in the above indications is the compound form of Example 1, i.e. substance A, i.e. the compound of formula I wherein the C* has the R configuration, namely 3-O-[N-acetylmuramyl-L-threonyl-D-isoglutaminyl]-1,2-di-O-palmitoyl-sn-glycerol.

Pharmaceutical compositions containing the compound of the invention together with at least one pharmaceutically acceptable carrier or diluent are also a part of the present invention. They may be prepared in conventional manner, e.g. according to a process comprising mixing the compound of the invention as defined above, i.e. the compound of formula I wherein the C* has the R or, respectively, the S configuration, with a pharmaceutically acceptable carrier or diluent.

Further pharmaceutical compositions which are indicated are in the form of liposomes and of mixed micelles with e.g. lysophosphatidyl choline, n-octyl glucose or deoxycholate. Such compositions may be prepared in conventional manner and be e.g. in the form of injectable solutions. They are also a part of the present invention.

The invention further includes a method of treatment, curative or supportive, of conditions as described above comprising administering to a subject in need of such treatment a therapeutically effective amount of the compound of the invention.

We claim:

1. The forms of the compound of formula I

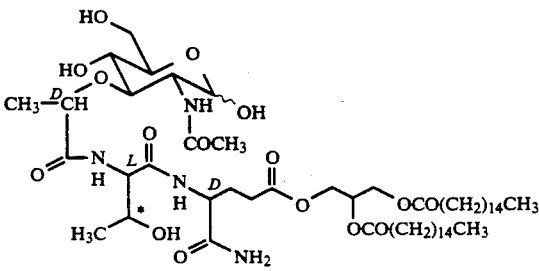

wherein the carbon atom marked with an asterisk * has the R or, respectively, the S configuration.

2. The compound according to claim 1 wherein the carbon atom marked with an asterisk * has the R configuration.

3. The compound according to claim 1 wherein the carbon atom marked with an asterisk * has the S configuration.

4. A pharmaceutical composition comprising the compound according to any one of claims 1 to 3 together with at least one pharmaceutically acceptable carrier or diluent.

5. A pharmaceutical composition according to claim 4 which is in liposomal form.

6. A pharmaceutical composition according to claim 4 which is in the form of mixed micelles.

7. A method of treating decreased immune response or suppressing IgE formation, which comprises administering a therapeutically effective amount of a compound of claim 1, 2, or 3 to a subject in need of said treatment.

* * * * *